United States Patent
Bernard et al.

(10) Patent No.: US 6,753,141 B2
(45) Date of Patent: Jun. 22, 2004

(54) SIMULTANEOUS SCREENING AND IDENTIFICATION OF SEQUENCE ALTERATIONS FROM AMPLIFIED TARGET

(75) Inventors: Philip S. Bernard, Salt Lake City, UT (US); Carl T. Wittwer, Salt Lake City, UT (US); Gregory Pritham, Easton, NH (US)

(73) Assignee: The University of Utah, Salt Lake City, UT (US)

( * ) Notice: Subject to any disclaimer, the term of this patent is extended or adjusted under 35 U.S.C. 154(b) by 20 days.

(21) Appl. No.: 09/770,770

(22) Filed: Jan. 25, 2001

(65) Prior Publication Data

US 2002/0142300 A1 Oct. 3, 2002

Related U.S. Application Data

(60) Provisional application No. 60/178,139, filed on Jan. 25, 2000.

(51) Int. Cl.⁷ .............................. C12Q 1/68; C12P 19/34
(52) U.S. Cl. ......................... 435/6; 435/91.1; 435/91.2; 935/77; 935/78
(58) Field of Search .......................... 435/6, 91.2, 91.1; 935/77, 78

(56) References Cited

U.S. PATENT DOCUMENTS 5,571,639 A    11/1996  Hubbell et al.
5,814,491 A    9/1998   Vijg et al.
6,054,270 A *  4/2000   Southern ................. 435/6

OTHER PUBLICATIONS

Abrams et al., Genomics 7:463–475 (1990).
Conner et al., Proc. Nat. Acad. Sci., 80:278–282 (1983).
Crockett AO, Wittwer CT. Anal Biochem. Mar. 1, 2001;290(1):89–97.
Gundry et al., *Genetic Testing* 3:365–370 (1999).
Lay and Wittwer, *Clin. Chem.* 43:2262–2267 (1997).
Mers et al., Methods Enzymol. 155:501–527 (1987).
Orita et al., Genomics 5:874–879 (1989).
Peyret et al., *Biochemistry* 38(12):3468–3477 (1999).
Ririe et al., *Anal. Biochem.* 245:154–160 (1997).
Santa Luci et al., *Proc. Nat. Acad. Sci. USA* 95:1460–1465 (1998).
Schutz et al., *BioTechniques* 27:1218–1224 (1999).
Wittwer et al., *BioTechniques* 22:176–181 (1997).

* cited by examiner

Primary Examiner—Jeffrey Siew
Assistant Examiner—Joyce Tung
(74) Attorney, Agent, or Firm—Dorsey & Whitney LLP; Richard F. Trecartin; Steven P. Lendaris

(57) ABSTRACT

Methods for identifying and locating alterations in a nucleic acid having a known sequence are provided. The methods involve measuring the melting temperature of probe nucleic acids hybridized to a target nucleic acid. The methods take advantage of the differential dissociation temperatures of a probe from a target resulting from mismatches at different locations along the region of the target to which the probe hybridizes.

16 Claims, 3 Drawing Sheets

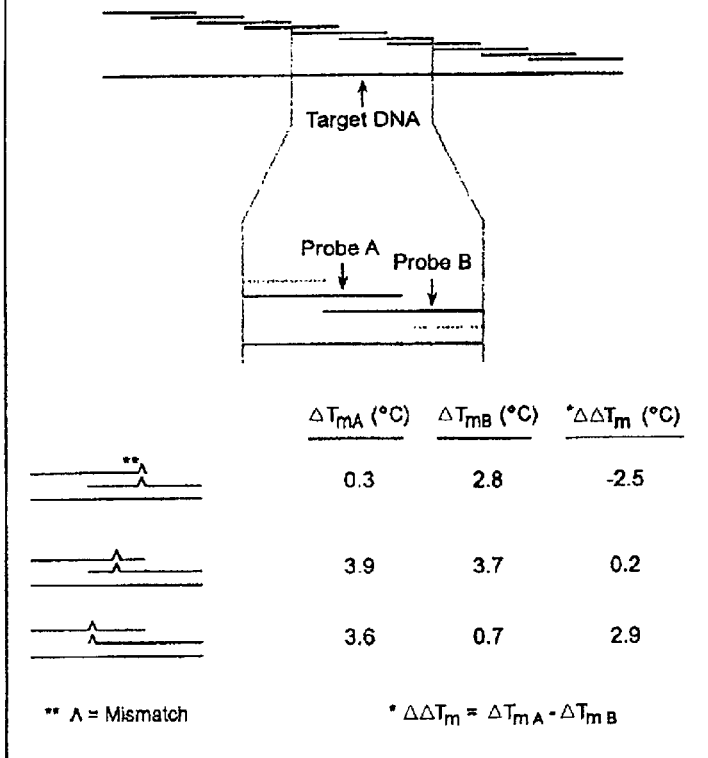
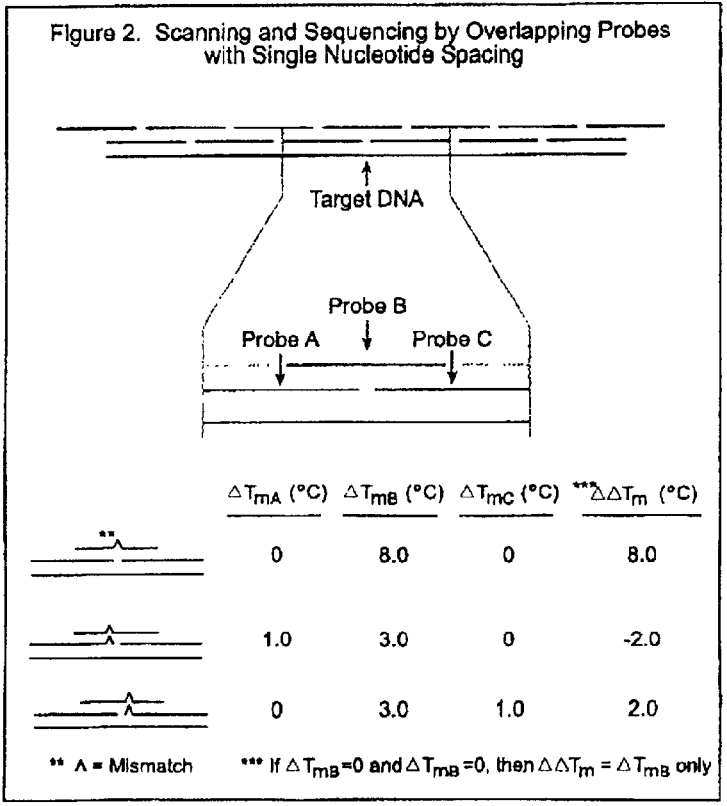

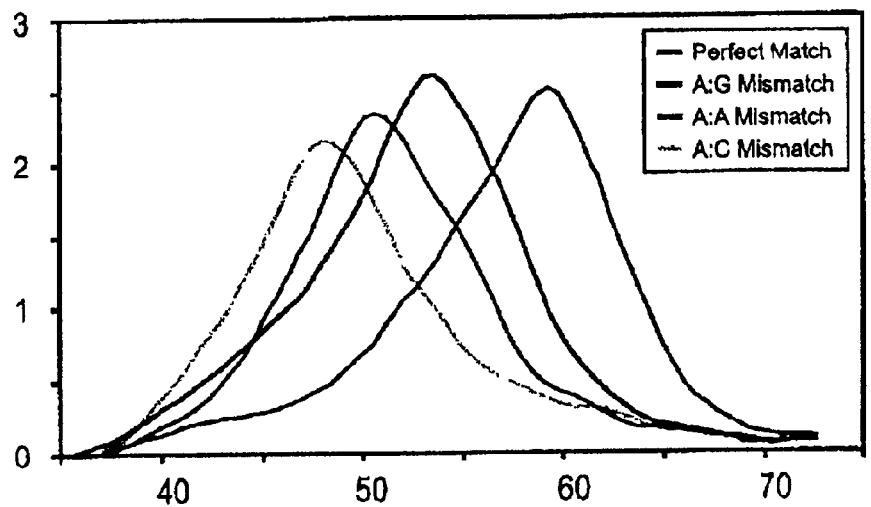
Figure 3. Effect on $T_m$ of Different Mismatches in the Center of a 15mer Duplex
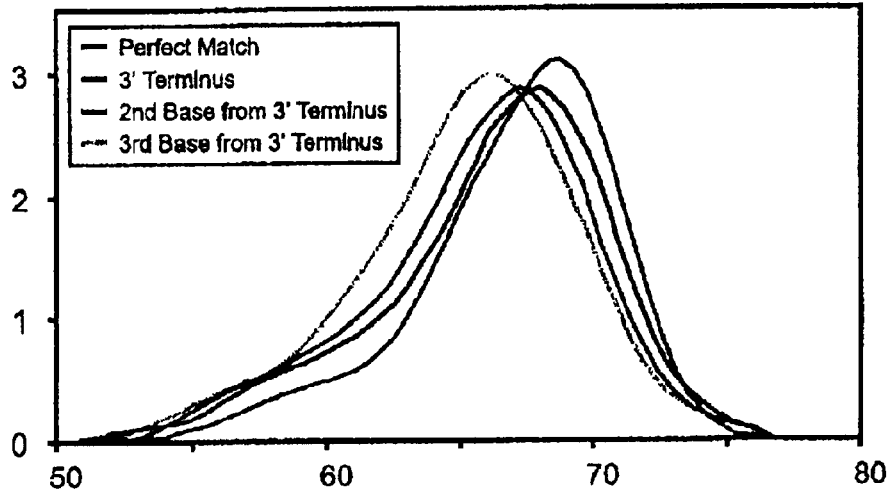
Figure 4. Effect of G:T Mismatch Position using 20mer Probes

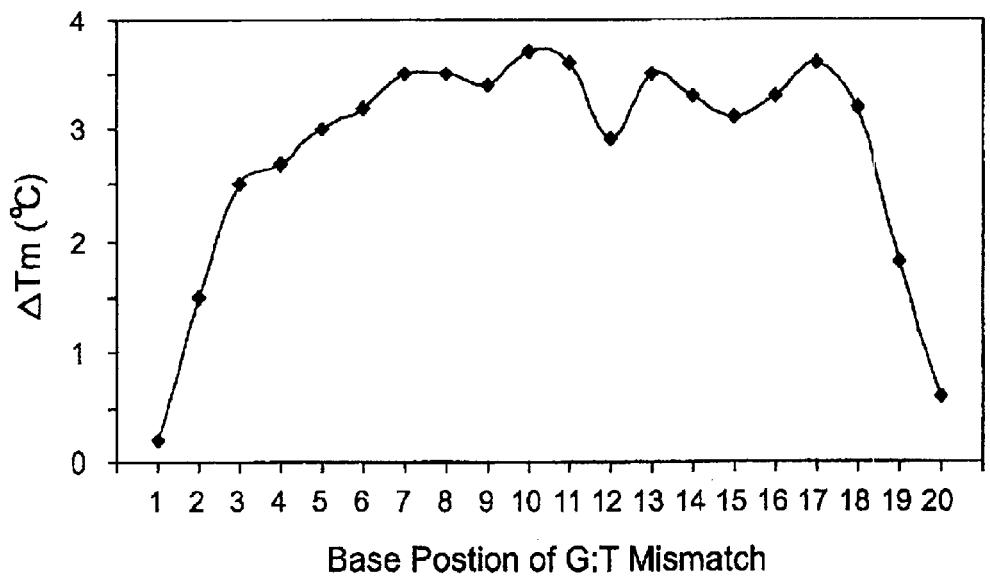
Figure 5. Tm Shift vs. Position of G:T Mismatch under a 20mer Probe
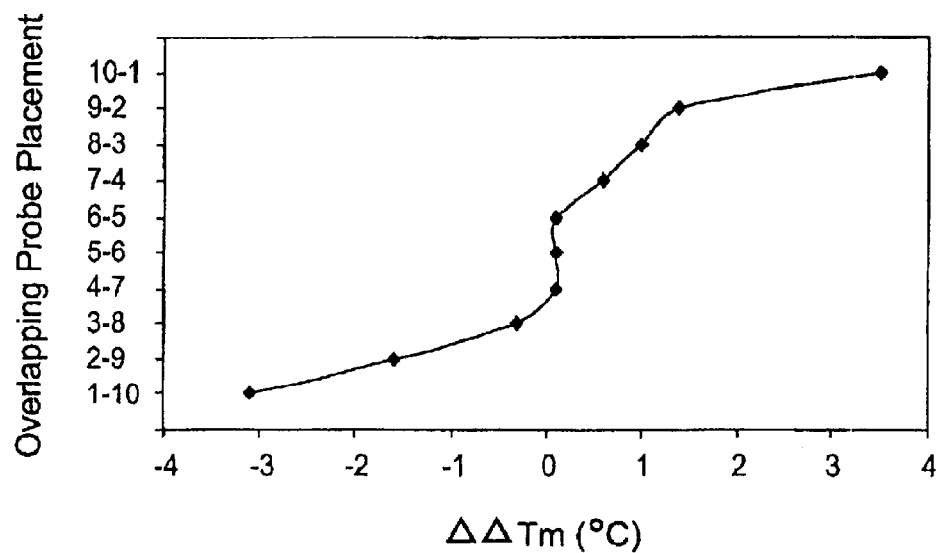
Figure 6. ΔΔTm of G:T Mismatches at Different Positions using the Overlapping Probe Embodiment

SIMULTANEOUS SCREENING AND IDENTIFICATION OF SEQUENCE ALTERATIONS FROM AMPLIFIED TARGET

This application claims the benefit of provisional application Serial No. 60/178,139, filed Jan. 25, 2000.

FIELD OF THE INVENTION

The invention relates to methods for screening for and identifying sequence alterations in nucleic acids.

BACKGROUND OF THE INVENTION

The ability to scan and identify sequence alterations has widespread applications in many areas including genetics, immunology, infectious disease, oncology, epidemiology and forensics. Mutations leading to cancer can arise in a number of different genes and in different positions within the same gene. Gene variants also can be the source of hereditary diseases. Scanning and identification of such nucleic acid alterations have important implications for diagnosis and prognosis and for guiding therapy.

Several methods exist for scanning for the presence or absence of sequence variants. Denaturing Gradient Gel electrophoresis (DGGE) takes advantage of differences in the melting location of slightly different nucleotide sequences on a gradient gel during electrophoresis. (Mers et al., Methods Enzymol. 155:501–527 (1987); Abrams et al., Genomics 7:463–475 (1990); Vijg et al., U.S. Pat. No. 5,814,491) The process is generally performed on fragments of a nucleic acid of interest produced through polymerase chain reaction (PCR). Similarly, differences in mobility during electrophoresis of single strands of nucleic acid is used in the technique known as Single-Strand Conformation Polymorphism (SSCP). (Orita et al., Genomics 5:874–879 (1989)) This method takes advantage of different conformations assumed by nucleic acids having slightly different sequences under non-denaturing conditions. But, while these methods can identify nucleic acid sequences with alterations, the nature and exact location of the alteration(s) must be subsequently determined by other techniques.

Identification of the location and nature of an alteration in a nucleic acid sequence may be determined by direct sequencing. However, this process is generally very labor intensive and time-consuming. Other means of detecting known sequence alterations involve the use of oligonucleotides which hybridize to the specific altered sequence. (Conner et al., Proc. Nat. Acad. Sci., 80:278–282 (1983)) This method becomes untenable, however, when an alteration is unknown. Other methods utilizing restriction enzymes have been developed to identify alterations in a sequence without directly sequencing the nucleic acid. Unfortunately, these enzymes recognize only a limited number of restriction sequences. And none of these methods provides for quick determination of which alteration is actually present.

It is apparent that there is a need for a fast and simple method of screening nucleic acids for alterations and determining the precise location and nature of such an alteration.

Accordingly, it is an object of the present invention to provide novel methods of screening for sequence alterations in a target nucleic acid. The invention provides methods utilizing probes which hybridize to nucleic acid to detect alterations in a target sequence as compared to a control.

It is a further object of the invention to provide methods of screening for and determining the location of a sequence alteration in a target nucleic acid in a single step. These methods utilize probes which hybridize to nucleic acid to detect the existence and location of alterations in a target sequence.

An additional object of the invention is to provide methods of screening, determining the location and determining the nature of a sequence alteration in a target nucleic acid in a single step. These methods provide for the identification of specific base changes in the target sequence.

SUMMARY OF THE INVENTION

In accordance with the objectives outlined above, the present invention provides methods of screening and identifying alterations in a target nucleic acid sequence as compared with a control nucleic acid. Probes are produced which are complementary to and, therefore, hybridize to overlapping regions of a control nucleic acid. The methods are based on the fact that probes directed to a control sequence denature from a target sequence at a different temperature than from the control when the target sequence has an alteration (such as a point mutation) as compared with the control at the location at which the probe hybridizes.

In one aspect of the present invention, a method is provided for identifying a sequence alteration in a target nucleic acid as compared to a control nucleic acid. The method entails hybridizing a plurality of nucleic acid probes with said target nucleic acid, wherein said probes are complementary to different overlapping regions of said control nucleic acid. The melting temperature ($T_m$) of at least two overlapping probes is determined, as well as the difference between the melting temperature of each probe from the target nucleic acid and the control nucleic acid ($\Delta T_m$). The difference between the $\Delta T_m$s of overlapping probes is determined as an indication of whether or not a sequence alteration exists in the target nucleic acid as compared to the control nucleic acid. In one embodiment, as few as two probes are required to examine a specific sequence alteration in target nucleic acid as compared with control nucleic acid.

In the method described above, the difference in $\Delta T_m$ between at least two overlapping probes indicates the location of a nucleotide difference in the target nucleic acid as compared to the control nucleic acid. In addition, the difference in $\Delta T_m$ between at least two overlapping probes indicates a substitution in the target nucleic acid sequence as compared to the control nucleic acid. Furthermore, the difference in $\Delta T_m$ between at least two overlapping probes indicates the type of nucleotide substituted in the target nucleic acid sequence as compared to the control nucleic acid.

In another aspect of the invention, provided herein is a method for identifying a sequence alteration in a target nucleic acid as compared to a control nucleic acid. The method involves hybridizing a plurality of nucleic acid probes with the target nucleic acid; a first set of probes is complementary to regions of the control nucleic acid separated by one or more nucleotides and at least a second set of probes is complementary to regions of the control separated by one or more nucleotides. The regions complementary to the second set of probes include the nucleic acids separating the first set of probes and are overlapping with the regions complementary to the first set of probes. The method further entails determining the melting temperature ($T_m$) of at least two overlapping probes from the target nucleic acid, determining for these at least two overlapping probes the difference between the $T_m$ from the target nucleic acid and the $T_m$ from the control nucleic acid ($\Delta T_m$), and determining the difference in determined $\Delta T_m$ between overlapping probes. The difference $\Delta T_m$ between overlapping probes provides an indication of the presence or absence of a sequence alteration in the target nucleic acid as compared to the control nucleic acid. Preferably only two sets of probes are used.

Further to the method just described, the difference in $\Delta T_m$ between at least two overlapping probes indicates the location of a nucleotide difference in the target nucleic acid as compared to the control nucleic acid. In addition, the difference in $\Delta T_m$ between at least two overlapping probes indicates a substitution in the target nucleic acid sequence as compared to the control nucleic acid. Furthermore, the difference in $\Delta T_m$ between at least two overlapping probes indicates the type of nucleotide substituted in the target nucleic acid sequence as compared to the control nucleic acid.

Also with respect to the method just described, in one embodiment only three probes are used, two from the first set which are complementary to adjacent regions and one from the second probe set which overlaps each of the probes from the first probe set. In this latest case, when the probes from the first probe set have a $\Delta T_m$ of zero and the probe from the second probe set has a $\Delta T_m$ other than zero, an alteration in the target is indicated as being in the nucleotides of the control nucleic acid sequence separating the regions to which the probes from the first probe set are complementary. In the case that one nucleotide separates adjacent regions to which the probes of the first probe set are complementary, a $\Delta T_m$ of zero for two adjacent (non-overlapping) probes and a $\Delta T_m$ other than zero for a probe which overlaps both adjacent probes indicated that the alteration is at the nucleotide separating the adjacent regions. In this last case, the $\Delta T_m$ of the overlapping probe indicates both a substitution as the sequence alteration and the type of substitution.

DESCRIPTION OF THE DRAWINGS

FIG. 1 depicts schematically how overlapping probes are walked along a complementary single-stranded target such that each probe shares a common sequence with a probe placed before and after it. This figure also shows actual experimental data illustrating the relative destabilization of overlapping probes in response to single nucleotide alterations in the target at different locations in the overlapping region.

FIG. 2 depicts an alternative embodiment of the present invention in which a set of probes are walked along the complementary target, separated by a single base between flanking probes, and a second set of probes is similarly walked along the target, separated by a single base and centered on the bases separating the first set of probes. This figure also presents predicted changes in melting temperature of adjacent and overlapping probes in response to a single base alteration in the target at different locations.

FIG. 3 shows the effects on the melting temperature of a 15 mer oligonucleotide probe from an otherwise complementary target in response to different nucleotide pairings at the center position of the probe. A Unique melting temperature is seen for each pairing.

FIG. 4 shows the effects on the melting temperature of a 20 mer probe from an otherwise complementary target in response to a single G:T mismatch at different locations along the length of the probe. A unique melting temperature is seen for each location.

FIG. 5 shows $\Delta T_m$ for G:T mismatches at 20 different positions within the hybridization region of a 20 mer probe to a target. This figure illustrates the increasing destabilization of a duplex as a G:T mismatch is moved from the end position of the probe to the center. At each position, $T_m$ was determined for a completely complementary duplex and the same duplex with a G:T mismatch.

FIG. 6 shows how the position of a mismatch can be localized using the $\Delta T_m$'s of 2 overlapping probes to determine $\Delta\Delta T_m$. The two probes had an overlapping hybridization region of 10 nucleotides on the targets. When the mismatch is positioned at a similar distance from the end of each probe, the $\Delta\Delta T_m$ is at or near zero. In comparison, if the mismatch is positioned near the end of one probe and the center of another, the $\Delta\Delta T_m$ is at its greatest. The direction of the $\Delta\Delta T_m$ sign (i.e., +or −) indicates at which end of the overlapping region the mismatch is positioned.

DETAILED DESCRIPTION OF THE INVENTION

The present invention provides methods of screening for and identifying sequence alterations in a target nucleic acid. These methods utilize probes which are complementary to a control nucleic acid. The temperature of thermal denaturation (melting) of these probes when hybridized with the target is compared with the melting temperatures of the same probes from the control. Surprisingly, determination of melting temperature of the individual probes from the target and the control provide sufficient information to determine not only the location of an alteration, but the nature of a nucleotide substitution. A difference in melting temperature of a probe detects an alteration and provides information about the nature of the alteration. Differences in melting temperatures of overlapping probes provides information to localize the alteration. Advantageously, the screening and identification of the sequence alteration can be obtained in a single thermal denaturation step.

It is contemplated that the present invention may be applied to virtually any nucleic acid for which the sequence is known. The methods are particularly useful for identifying single nucleotide substitutions in a target.

By "melting temperature" ($T_m$) is meant the temperature at which a probe dissociates from a nucleic acid to which it is hybridized under defined conditions. The conditions are preferably chosen so as to provide the maximum change in $T_m$ if a mismatch is present. Examples of preferred hybridization conditions are conditions used for asymmetric amplification by PCR, so that no sample handling is necessary. The same solution can then be amplified and melted in the same instrument to determine $T_m$ values. An example of asymmetric amplification and melting analysis is found in Lay and Wittwer, *Clin. Chem.* 43:2262–2267 (1997), which is incorporated herein in its entirety. In one embodiment of the present invention, asymmetric amplification is used to produce an excess of one strand of a target or control, so that the overproduced product hybridizes to the probes rather than to its complementary product strand.

In another embodiment of the invention, single strand production and melting analysis is performed as separate steps. Single strand nucleic acid may be produced by asymmetric PCR or other techniques known in the art. Examples of such techniques include self sustained sequence replication (3SR) and strand displacement amplification (SDA). The single strand target or control is then combined with the probes and $T_m$ values are determined. In this embodiment, any probe hybridization solution may be used, such solutions being well known in the art.

By "probe" is meant any sequence of molecules which is complementary to the control. By "complementary" is meant that the probe has a specific sequence of molecules which specifically hybridizes on a residue-by-residue basis with a sequence of nucleic acid. Such molecules include nucleic acids like DNA or RNA, and probes can contain both deoxy- and ribonucleic acids (oligonucleotides). The probes may have a ribose-phosphate backbone typical of naturally occurring DNA or RNA, but may also contain modifications in such a ribose-phosphate backbone. Probes may also be in other forms, for example as peptide nucleic acids.

Means for producing probes having a desired sequence are well known in the art. Preferably, each probe has the same number of nucleotides. Preferably, each probe is between 10 and 50 nucleic acids in length, more preferably between 10 and 30 nucleic acids, still more preferably, from 15 to 20 nucleic acids. In one embodiment, each probe is a 15-base nucleic acid. In another embodiment, each probe is a 20-base nucleic acid.

In one embodiment of the invention, the probes are completely overlapping. By "overlapping" is meant that at least two probes hybridize with the same one or more nucleotides of the control nucleic acid. This embodiment will be referred to as the complete overlapping embodiment. In a preferred embodiment, any one nucleotide of the control is in the hybridizing region of exactly two probes.

In another embodiment, a set of probes is complementary to regions of the control nucleic acid such that at least one nucleotide of the control separates each adjacent region, therefore a spacing of at least one nucleotide separates each adjacent probe in the set when hybridized. In this embodiment, at least a second set of probes similarly is complementary to regions of the control such that at least one nucleotide separates each adjacent region, each probe of the second being complementary to a region of the control containing the one or more nucleotides which separate adjacent probes of the first set. This will be referred to as the nucleotide spacing embodiment. In a preferred embodiment, a single nucleotide separates each adjacent region in each probe set.

Any means of determining the melting temperature of a probe may be used. Several means of determining the melting temperature of hybridized nucleotides are known in the art.

In a preferred embodiment, fluorescent double-stranded DNA specific dyes are used to determine the melting temperature. In this embodiment, the fluorescent output of a sample of probe hybridized with target or control is monitored as the sample is heated. The fluorescent output is plotted against the temperature to determine the melting temperature of the probe from the target or control.

In another preferred embodiment, probes comprising a fluorescent label are used. For example, the hybridization of 5'-fluorescein-labeled probes, and melting thereof, can be observed when the fluorescein label is in close proximity to a guanosine residue on the complementary strand, due to the inherent quenching of fluoresceine signal by guanosine. (See, Crocket and Wittwer, Anal. Biochem., in press (2001), incorporated herein in its entirety).

A difference in melting temperature of a probe from the target as compared with the melting temperature of an identical probe from the control ($\Delta T_m$) indicates an alteration in the target sequence as compared to the control. A $\Delta T_m$ of a second probe localizes the alteration to the region of the target in which the two probes overlap. The difference between $\Delta T_m$ of two overlapping probes ($\Delta \Delta T_m$) indicates the exact position of the base change in the overlapping region because this number is unique for each residue location for each type of residue change, as further described below.

The magnitude of $\Delta T_m$ for a given probe also indicates the nature of a base change which is present. That is, the type of residue (e.g., adenine, guanosine, thymine, cytosine) that is different in the target as compared with the control may be determined. In a preferred embodiment, determination of the residue change in a target as compared to a control is made using a $T_m$ profile map, as further described below. A "$T_m$ profile map" is a table describing the anticipated $\Delta T_m$ for each possible residue change under consideration for each residue with which a probe hybridizes. The $T_m$ profile map may be generated from experimental data for specific sequence alterations in a control sequence or from predicted $T_m$'s using thermodynamic calculations (See, Santa Luci et al., Proc. Nat. Acad. Sci. USA 95:1460–1465 (1998) and Schutz et al., BioTechniques 27:1218–1224 (1999)).

In a preferred embodiment, determination of the residue change in a target as compared to a control is made using $\Delta T_m$ of two or more probes. Example 3 further illustrates determination of the location and type of a single nucleotide change in a target as compared to a control.

In a preferred embodiment, the rate at which the temperature is increased during the determination of a melting temperature for a probe is the same for all probes and for each probe in determining the melting temperature from the target and from the control. In an alternate embodiment, the melting temperature for a probe of interest from a given target is determined at two or more rates of increasing temperature.

In a preferred embodiment, melting temperatures of a probe from one or more targets having known alterations are determined to produce a $T_m$-alteration profile or $\Delta T_m$ map for the probe. A "$T_m$ profile map" is a table describing the anticipated $\Delta T_m$ for each possible residue change under consideration for each residue with which a probe hybridizes. The $T_m$ may be determined for alterations at different locations, as well as alterations involving different nucleotide substitutions. Additionally, the $T_m$ for each of two or more different rates of increasing temperature may be determined for one or more alterations, to produce a $T_m$-alteration-rate profile. The $T_m$ profile map may also be generated from predicted $T_m$'s using thermodynamic calculations, as is well known in the art. (See, Santa Luci et al., Proc. Nat. Acad. Sci. USA 95:1460–1465 (1998); Schutz et al., BioTechniques 27:1218–1224 (1999); and Peyret et al., Biochemistry 38(12):3468–3477 (1999), each of which is incorporated herein in its entirety).

The differences in $\Delta T_m$ between the two probes is used to determine the location within the overlap region of the two probes. Alternatively, the $\Delta T_m$ for each probe may be determined at two or more rates of increasing temperature.

In the single nucleotide spacing embodiment using two sets of probes, usually two probes will hybridize to the region having any single base mutation and each of said probes will have a $\Delta T_m$. However, in the case where a single base change occurs in the gap between the hybridization region of two probes of one probe set, only one probe of the other probe set will have a $\Delta T_m$. Otherwise, when the $\Delta T_m$ of a first probe is subtracted from the $\Delta T_m$ of a second overlapping probe, the difference in $\Delta T_m$ between the overlapping probes ($\Delta \Delta T_m$) will increase for each alteration that is closer to the end of the first probe. Alternatively, the location of the alteration may be determined from the $\Delta T_m$-alteration-rate profile for either or both of the first and second probes.

In addition to the location of the alteration, the nature of a nucleotide substitution may be determined as described above. In one embodiment, a $T_m$-alteration profile for one or both overlapping probes with a $\Delta T_m$ is used to determine the substitution.

In one embodiment, the invention is implemented in a nucleotide solid support array. Such arrays are well known in the art. An example of such an array is described in U.S. Pat. No. 5,571,639, incorporated herein in its entirety.

In a preferred embodiment, the determination of the $T_m$ of the probes for a given target and control is done simultaneously.

In a preferred embodiment, the invention is automated. In this embodiment specialized hardware and software programs may be applied to control the automation of the invention. One system useful in the present invention is the commercially available LightCycler™, made by Idaho Technology (Wittwer et al., *BioTechniques* 22:176–181 (1997), incorporated herein in its entirety). This apparatus is capable of rapid thermal cycling necessary for amplification of nucleic acid for procedures such as PCR. This apparatus is also capable of providing a probe/control and/or probe/target sample with a prescribed temperature within a very broad range and change temperatures at a prescribed rate. The LightCycler™ is also capable of measuring fluorescence in a sample and changes in fluorescence coincidentally with changing temperature for $T_m$ determinations.

The present invention finds uses in many fields, including but not limited to genetics, immunology, infectious disease, oncology, epidemiology and forensics. Such uses include, but are not limited to, identifying mutations in tumorigenic material, identifying inheritable genetic disease and guiding treatment for such diseases. Additionally, the invention may be used for identifying allelic variants, identifying sources of biological samples and determining paternity.

It will be apparent to one of ordinary skill in the art that many other applications of the present invention are possible. All references cited herein are incorporated in their entirety.

The following examples are provided for illustrative purposes. It is understood that these examples in no way serve to limit the true scope of the invention.

EXAMPLES

Example 1

Asymmetric PCR is performed by rapid cycling techniques in a reaction volume of 10 µl with dNTP's at 200 µM each, one primer at 0.5 µM, the other primer at 0.05 µM, 3 mM $Mg^{2+}$, 50 mM Tris (pH 8.3), 500 mg/ml BSA. 0.4 U Taq polymerase, and 10 ng of genomic DNA. After 50 cycles of 94° C. for 0 seconds, 55° C. for 0 seconds and 72° C. for 10 seconds, the sample is cooled to 40° C. and a high resolution melting curve is performed by heating at 0.05° C. per second in the presence of fluorescent double-stranded DNA-specific dye.

Melting curves are acquired for all probes and the first derivative of each curve is calculated and plotted as –dF/dT (the negative first derivative of fluorescence with respect to temperature). $T_m$s are determined as the peak of each derivative curve by Gaussian fitting. $\Delta T_m$'s (the difference in $T_m$ between control and test samples) and $\Delta\Delta T_m$s (the difference in $\Delta T_m$ when using different probes) are calculated and used to identify sequence alterations in the test sample as compared to the control sample.

Example 2

Single stranded nucleic acid of a control and a target are separately produced by asymmetric PCR, SDA or 3SR. After amplification with a biotinylated primer, the amplified control and target are purified by attachment to streptavidin-coated magnetic beads. The purified single strand nucleic acid is placed in probe wells or a probe chip and analyzed by melting as in Example 1.

Example 3

Single Nucleotide Polymorphism (SNP) Screening and Identification.

Two sets of 15-mer nucleic acid probes are produced for use in the nucleotide spacing embodiment described above, wherein the number of nucleotides separating adjacent complementary regions for each probe set is one (see FIG. 2). If a $\Delta T_m$ is observed for only one probe then the SNP is localized to the specific base that is unique for that probe. The magnitude of $\Delta T_m$ identifies the specific base change (see FIG. 3). If a $\Delta T_m$ is observed for two probes, then the SNP is localized to the base positions where the overlap between probes occurs. The specific position and base change is identified from a Tm alteration profile map that is either measured experimentally or predicted from thermodynamic calculations (SantaLucia, *Proc. Nat. Acad. Sci. USA*, 95:1460–1465 (1998); Schutz et al., *BioTechniques*, 27:1218–1224 (1999)).

An example of a partial $T_m$ alteration profile for the overlapping portion of 2 probes is shown in Table 1. There are seven possible positions that overlap between these 15-mer probes. The partial $T_m$ alteration map of Table 1 shows all possibilities for SNP changes for an A in the control DNA (a complete map would contain 3 other Tables of equal size for C, G, and T, but the principle is the same). The values of $\Delta T_m(1)$, $\Delta T_m(2)$, and $\Delta\Delta T_m$ in the Table are used to identify the position and precise SNP that is present.

TABLE 1

Sequence Map for base A in the control sequence

| | Position | | | | | | | |
|---|---|---|---|---|---|---|---|---|
| | 1 | 2 | 3 | 4 | 5 | 6 | 7 | Mismatch |
| $\Delta T_m(1)$ | 5 | 5 | 5 | 5 | 4 | 3 | 1 | A:G |
| $\Delta T_m(2)$ | 1 | 3 | 4 | 5 | 5 | 5 | 5 | |
| $\Delta\Delta T_m$ | 4 | 2 | 1 | 0 | −1 | −2 | −4 | |
| $\Delta T_m(1)$ | 10 | 10 | 10 | 10 | 8 | 6 | 2 | A:C |
| $\Delta T_m(2)$ | 2 | 6 | 8 | 10 | 10 | 10 | 10 | |
| $\Delta\Delta T_m$ | 8 | 4 | 2 | 0 | −2 | −4 | −8 | |
| $\Delta T_m(1)$ | 8 | 8 | 8 | 8 | 7 | 4 | 2 | A:T |
| $\Delta T_m(2)$ | 2 | 4 | 7 | 8 | 8 | 8 | 8 | |
| $\Delta\Delta T_m$ | 6 | 4 | 1 | 0 | −1 | −4 | −6 | |

With high-resolution determination of the $T_m$s, every possible SNP (there are 84 possibilities in the 7 positions, 21 are shown in Table 1) can be identified by a unique value of $\Delta T_m(1)$, $\Delta T_m(2)$, and $\Delta\Delta T_m$. Seldom is such precision required, and often the need is to distinguish between several sequence possibilities. In this case, a limited sequence map can be construction with only the sequence alterations that need to be screened. In this case, lower resolution equipment can be used to discriminate between the possibilities (not necessarily limited to SNPs). Another method to increase discrimination is to use different melting temperature rates (for example 0.1° C./sec and 0.5° C./sec to estimate $T_m$ (Ririe et al., *Anal. Biochem.* 245:154–160 (1997), incorporated herein in its entirety). Alternately, both heating and cooling curves can be obtained to estimate $T_m$ by melting and annealing (Gundry et al., *Genetic Testing* 3:365–370 (1999), incorporated herein in its entirety). When 2 different apparent $T_m$s are measured for each probe/target

We claim:

1. A method of identifying a sequence alteration in a target nucleic acid as compared to a control nucleic acid, said method comprising:
   a) hybridizing a plurality of nucleic acid probes with said target nucleic acid, wherein said probes are complementary to different overlapping regions of said control nucleic acid;
   b) determining the melting temperature ($T_m$) of at least two overlapping probes from said target nucleic acid;
   c) determining the $\Delta T_m$ for each of said overlapping probes, wherein the $\Delta T_m$ is the difference between the $T_m$ of said target nucleic acid and one of said overlapping probes and the $T_m$ of said control nucleic acid and the same overlapping probe; and
   d) determining the $\Delta\Delta T_m$, wherein the $\Delta\Delta T_m$ is the difference, if any, in the $\Delta T_m$ of at least two overlapping probes, as an indication of the presence or absence of a sequence alteration in said target nucleic acid as compared to said control nucleic acid.

2. The method of claim 1, wherein the $\Delta\Delta T_m$ indicates the location of a nucleotide difference in the target nucleic acid as compared to the control nucleic acid.

3. The method of claim 1, wherein the $\Delta\Delta T_m$ indicates a substitution in the target nucleic acid sequence as compared to the control nucleic acid.

4. The method of claim 3, wherein the $\Delta\Delta T_m$ indicates the type of nucleotide substituted in the target nucleic acid sequence as compared to the control nucleic acid.

5. The method of claim 3 or 4, wherein the $\Delta\Delta T_m$ indicates the location of the substitution in the target nucleic acid sequence as compared to the control nucleic acid.

6. A method of identifying a sequence alteration in a target nucleic acid as compared to a control nucleic acid, said method comprising:
   a) hybridizing at least a first and second set of nucleic acid probes with said target nucleic acid, wherein the members of said first set of probes are complementary to regions of said control nucleic acid separated by one or more nucleotides and the members of said second set of probes are complementary to regions of said control separated by one or more nucleotides, wherein the regions complementary to said second set of probes include the nucleotides separating the first set of probes and are overlapping with the regions complementary to said first set of probes;
   b) determining the melting temperature ($T_m$) of at least two overlapping probes from said target nucleic acid;
   c) determining the $\Delta T_m$ for each of said overlapping probes, wherein the $\Delta T_m$ is the difference between the $T_m$ of said target nucleic acid and one of said overlapping probes and the $T_m$ of said control nucleic acid and the same overlapping probe; and
   d) determining the the $\Delta\Delta T_m$, wherein the $\Delta\Delta T_m$ is difference in $\Delta T_m$, if any, of at least two overlapping probes, as an indication of the presence or absence of a sequence alteration in said target nucleic acid as compared to said control nucleic acid.

7. The method of claim 6, wherein only two sets of probes are used.

8. The method of claim 6, wherein the $\Delta\Delta T_m$ indicates the location in the control nucleic acid of a nucleotide difference between the target nucleic acid and the control nucleic acid.

9. The method of claim 6, wherein the $\Delta\Delta T_m$ indicates a substitution in the sequence of the control nucleic acid.

10. The method of claim 9, wherein the $\Delta\Delta T_m$ indicates the type of nucleotide substituted in the sequence of the control nucleic acid.

11. The method of claim 9 or 10, wherein the $\Delta\Delta T_m$ indicates the location of the substitution in the sequence of the control nucleic acid.

12. The method of claim 6, wherein $\Delta T_m$ is determined for at least two probes of said first set of probes which are complementary to adjacent regions of said control nucleic acid and at least one probe of a second set of probes which overlaps with each of said at least two probes of said first set of probes.

13. The method of claim 12, wherein a $\Delta T_m$ of zero for said at least two probes of said first set of probes and a $\Delta T_m$ of greater than zero for said at least one probe of a second set of probes indicates the location of a sequence alteration in the target nucleic acid as compared to the control nucleic acid at a nucleotide in the control nucleic acid separating the regions to which said at least two probes of said first set of probes are complementary.

14. The method of claim 13, wherein the regions of said control to which said first set of probes is complementary are separated by a single nucleotide and the location of said sequence alteration is at said single nucleotide.

15. The method of claim 14, wherein the $\Delta T_m$ of said at least one probe of a second set of probes indicates a substitution in the sequence of the control nucleic acid.

16. The method of claim 15, wherein the $\Delta T_m$ of said at least one probe of a second set of probes indicates the type of nucleotide substituted in the sequence of the control nucleic acid.

* * * * *

UNITED STATES PATENT AND TRADEMARK OFFICE
CERTIFICATE OF CORRECTION

PATENT NO. : 6,753,141 B2
DATED : June 22, 2004
INVENTOR(S) : Benard et al.

It is certified that error appears in the above-identified patent and that said Letters Patent is hereby corrected as shown below:

Column 1,
Line 7, add the following statement:
-- This invention was made with government support under Grant Number R41 GM 58983 awarded by the National Institutes of Health. The Government had certain rights to this invention. --

Signed and Sealed this

First Day of February, 2005

JON W. DUDAS
*Director of the United States Patent and Trademark Office*